United States Patent
Flynn

(10) Patent No.: US 7,219,668 B2
(45) Date of Patent: May 22, 2007

(54) MANUALLY-OPERABLE RESUSCITATORS

(76) Inventor: Stephen Flynn, 1055 Industry Street, Oakville, Ontario (CA) L6J 2X3

( * ) Notice: Subject to any disclaimer, the term of this patent is extended or adjusted under 35 U.S.C. 154(b) by 643 days.

(21) Appl. No.: 10/613,150

(22) Filed: Jul. 7, 2003

(65) Prior Publication Data
US 2004/0094150 A1    May 20, 2004

Related U.S. Application Data

(60) Provisional application No. 60/395,309, filed on Jul. 12, 2002.

(51) Int. Cl.
A61M 16/00    (2006.01)

(52) U.S. Cl. ............................ 128/205.13; 128/205.17; 128/203.28

(58) Field of Classification Search ........... 128/205.13, 128/205.14, 205.15, 205.16, 205.17, 205.18, 128/205.19, 202.28, 202.29, 203.11, 203.12, 128/203.28, 200.23, 203.15, 200.22, 207.14, 128/207.16
See application file for complete search history.

(56) References Cited

U.S. PATENT DOCUMENTS

| 4,374,521 | A | * | 2/1983 | Nelson et al. | 128/205.13 |
| 5,357,946 | A | * | 10/1994 | Kee et al. | 128/200.24 |
| 5,722,394 | A | * | 3/1998 | Loescher | 128/205.24 |
| 5,842,467 | A | * | 12/1998 | Greco | 128/200.23 |
| 6,158,428 | A | * | 12/2000 | Mecikalski | 128/200.23 |
| 6,276,363 | B1 | * | 8/2001 | Gray | 128/205.13 |
| 6,340,023 | B2 | * | 1/2002 | Elkins | 128/200.21 |

* cited by examiner

Primary Examiner—Justine R. Yu
Assistant Examiner—Amadeus Lopez
(74) Attorney, Agent, or Firm—Robert F. Delbridge

(57) ABSTRACT

A manually-operable resuscitator operable also to inject medication into air being supplied to a patient. The resuscitator has a resiliently compressible air bag having an inlet and an outlet. The inlet has a one-way valve through which air passes into the bag from the atmosphere and a patient valve through which air flows in passing from the bag to the patient. The patient valve has a one-way valve member through which air flows in passing from the bag to the patient. The patient valve also has a passage extending from the atmosphere to the interior thereof adjacent to the one-way valve member and upstream thereof through which medication can be injected into the air as it passes from the bag to the one-way valve member.

2 Claims, 4 Drawing Sheets

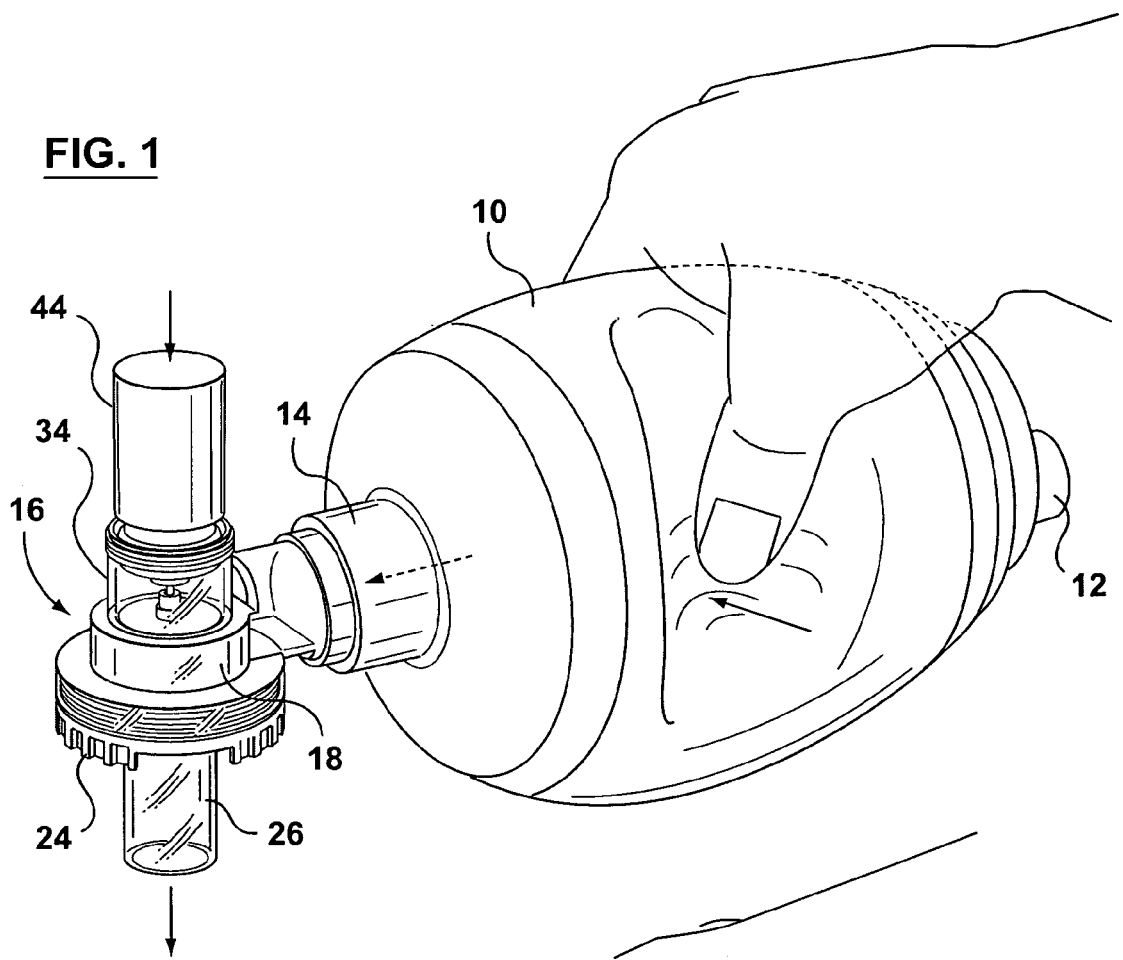
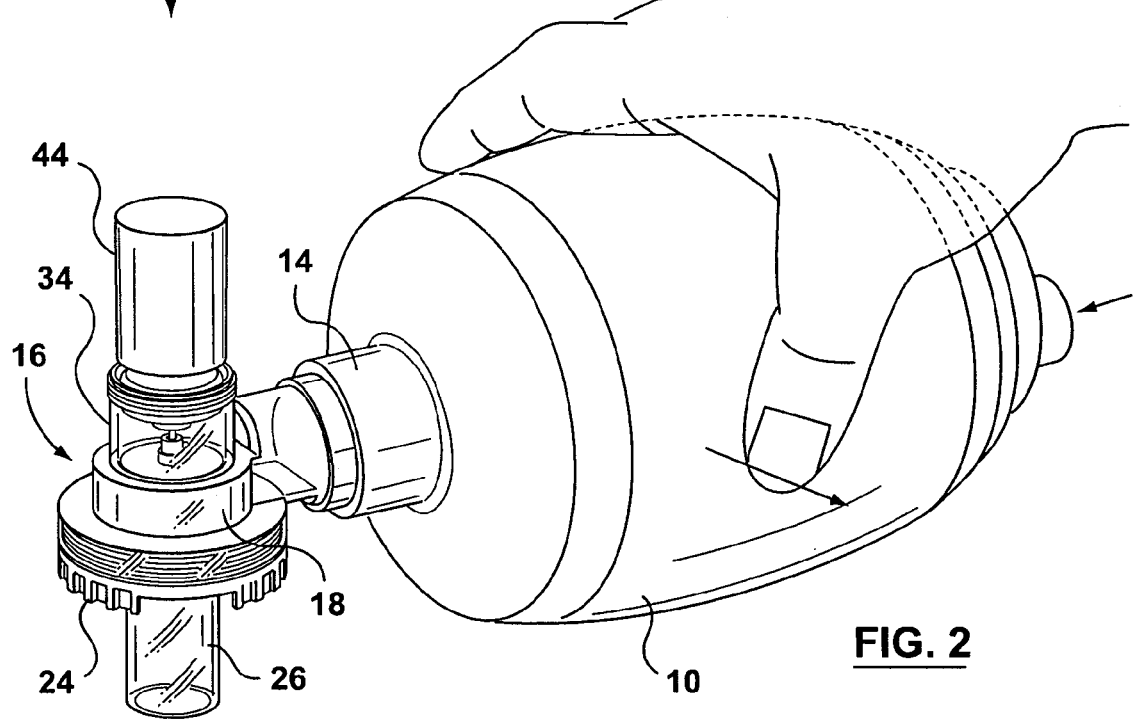

MANUALLY-OPERABLE RESUSCITATORS

RELATED APPLICATION

This invention claims priority from U.S. Provisional Patent Application No. 60/395,309 filed Jul. 12, 2002.

FIELD OF INVENTION

This invention relates to manually-operable resuscitators, and in particular to manually-operable resuscitators which also have provision for injecting medication into the air being supplied to a patient.

BACKGROUND OF INVENTION

A manually-operable resuscitator of this kind is shown in U.S. Pat. No. 5,791,340 (Schleufe et al.) wherein medication is injected into the rear end of the bag. However, this provision for injecting medication into the air being supplied to the patient is not particularly efficient because some of the medication may remain in the resuscitator bag and hence not reach the patient.

It is therefore an object of this invention to provide an improved resuscitator of this kind which substantially overcomes the problem mentioned above.

SUMMARY OF INVENTION

According to the present invention, a manually-operable resuscitator operable also to inject medication into air being supplied to a patient as a resiliently compressible air bag having an inlet and an outlet, the inlet having a one-way valve through which air passes into the bag from the atmosphere and a patient valve through which air flows in passing from the bag to the patient. The patient valve has a one-way valve member through which air flows in passing from the bag to the patient, and also has a passage extending from the atmosphere to the interior thereof adjacently one way valve member and upstream thereof through which medication can be injected into the air as it passes from the bag to the one way valve member and then to the patient.

Thus, with a resuscitator in accordance with the invention, substantially all the injected medication reaches the patient because none remains in the air bag. The passage may be provided with a one-way valve through which the medication passes. Also, the patient valve may cause the air from the bag to turn through approximately 90° to pass through the one-way valve member, the passage being located so as to inject medication into the air in a direction substantially parallel to the direction flow of the air through the one-way valve member.

DESCRIPTION OF THE DRAWINGS

One embodiment of the invention will now be described, by way of example, with reference to the accompanying drawings, of which:

FIG. 1 is a perspective view of a manually-operable resuscitator in accordance with one embodiment of the invention, with the air bag being squeezed to force air in through a patient valve;

FIG. 2 is a similar view but with the squeezing force having been released to enable air to be drawn into the air bag through an inlet bag;

DESCRIPTION OF PREFERRED EMBODIMENT

Figure 3:
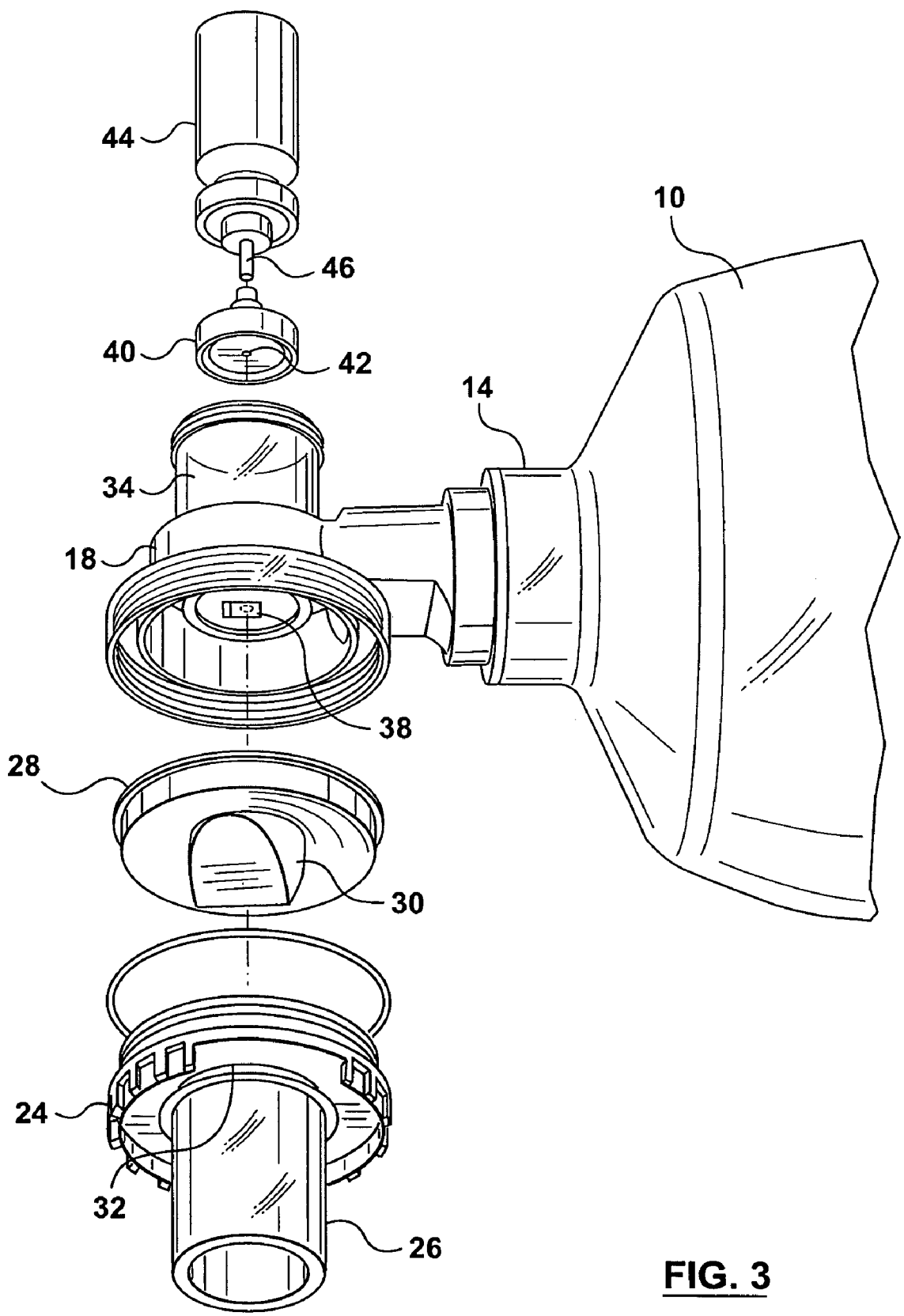
FIG. 3 is an exploded view of the patient valve with provision for supply of medication thereto in accordance with the invention.

Referring to the drawings, a manually-operable resuscitator has a resiliently compressible flexible air bag 10 with an inlet 12 and an outlet 14. Inlet 12 contains a conventional one-way inlet valve (not shown), the nature of which will be readily apparent to a person skilled in the art. The outlet 14 is provided with a patient valve 16 in accordance with the invention.

The patient valve 16 has an upper tubular part 18 with a horizontally extending inlet 20 which fits in the outlet 14 of the air bag 10 and a vertically downwardly extending outlet 22. The patient valve 16 also has a lower tubular part 24, the upper portion of which has an external screw thread which engages an internal screw thread at the outlet of the upper tubular portion 18 to secure the lower tubular portion 24 thereto. The lower tubular portion 24 has a central tubular member 26 whose upper end supports an intermediate portion of a flexible valve member 28 whose outer periphery is clamped between the upper and lower tubular portions 18, 24. The valve member 28 has a central duckbill portion 30 located in the central tubular member 26. The lower tubular portion 24 has apertures 32 surrounding the central tubular member 26.

As so far described, the patient valve is conventional and its manner of operation will be readily apparent to a person skilled in the art, particularly in view of the description which follows.

Figure 4:
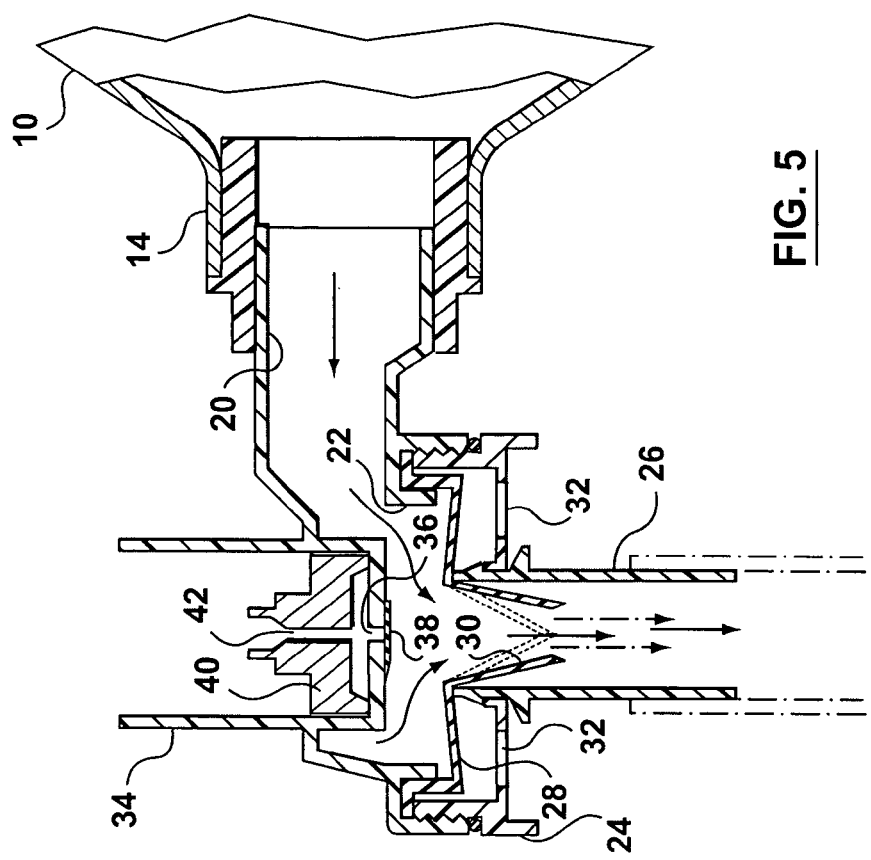
FIG. 4 is a sectional view of the patient valve in the closed condition.
Figure 5:
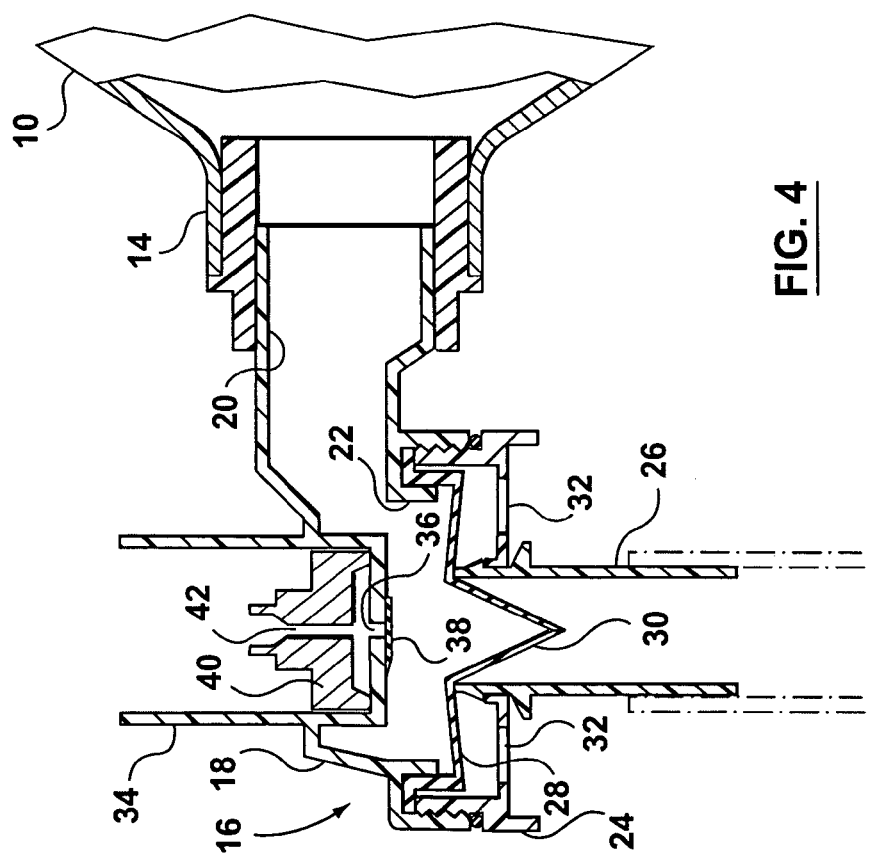
FIG. 5 is a similar view but with the patient valve in the open position enabling supply of air to a patient.

The flexible valve member 28 is normally in the closed condition shown in FIG. 4. When the air bag 10 is squeezed in the manner indicated in FIG. 1, the resultant air pressure opens the duckbill portion 30 of the valve member 28 as shown in FIG. 5 so that air flows from the air bag 10 through the patient valve 16 and out of the lower end of the central tubular member 26 which, in use, is connected in known manner with a patient's airway.

When squeezing of the air bag 10 ceases, as indicated in FIG. 2, pressure in the air bag 10 folds as it resiliently expands to its original shape, the duckbill portion 30 shuts and fresh air is drawn into the air bag 10 through the inlet 12 in known manner. When the patient exhales, therefrom the patient passes up the central tubular member 26 pushes the valve member 28 upwardly from the upper end thereof and passes into the atmosphere through the apertures 32.

In accordance with the invention, the upper tubular portion 18 of the patient valve 16 has provision for supplying medication directly to the duckbill valve portion 30 of the valve member 28. The upper tubular portion 18 has a vertically extending tubular medication container receiver 34 positioned so that it is directly vertically above the duckbill valve portion 30. The container receiver 34 is open at the top and it is closed at the bottom except for a small central aperture 36 normally closed by a flap valve 38. A connector 40 with a central passage 42 is located in the lower end of the container receiver 34 for a purpose which will become apparent from the following description.

If during use of the resuscitator it is desired to inject medication into the air being provided to the patient, a conventional medication aerosol container 44 is inserted into the container receiver 34 so that its outlet tube 46 communicates with the central passage 42 of the connector 40 and subsequently with the aperture 36.

Figure 7:
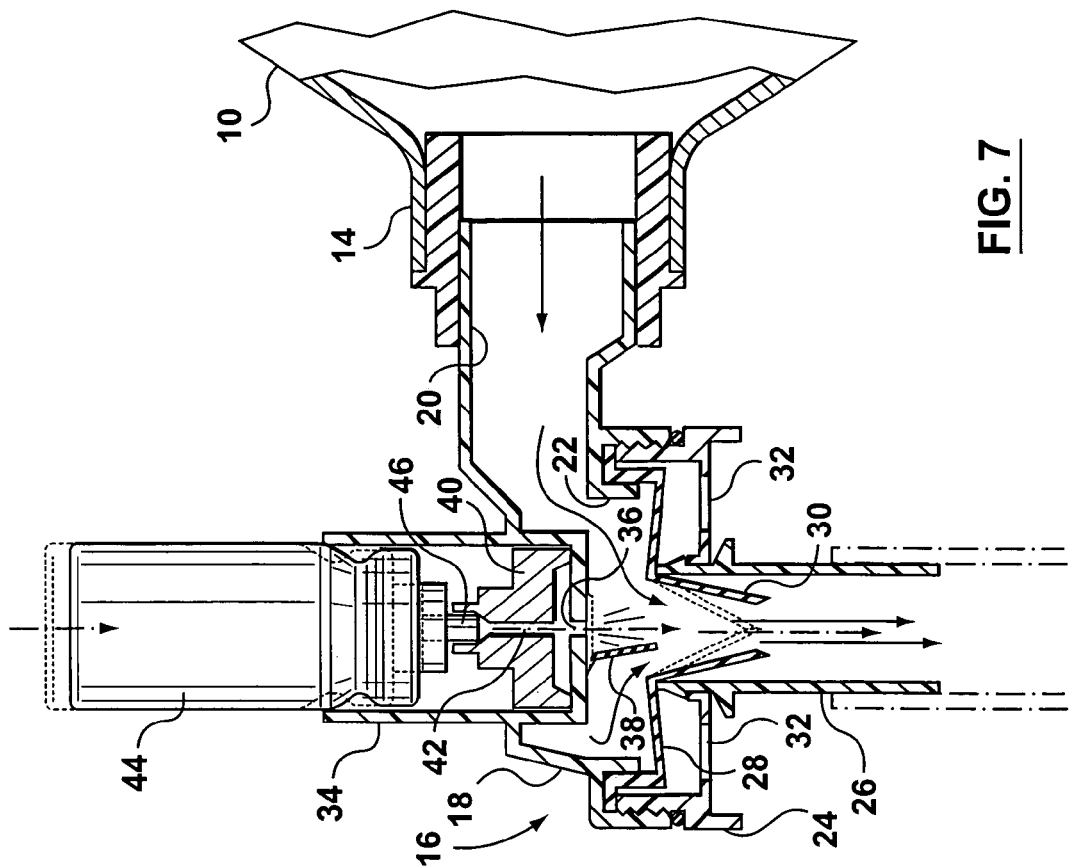
FIG. 7 is a similar view to FIG. 5 but also showing a medication container supplying medication directly into the inlet of the patient valve.
Figure 6:
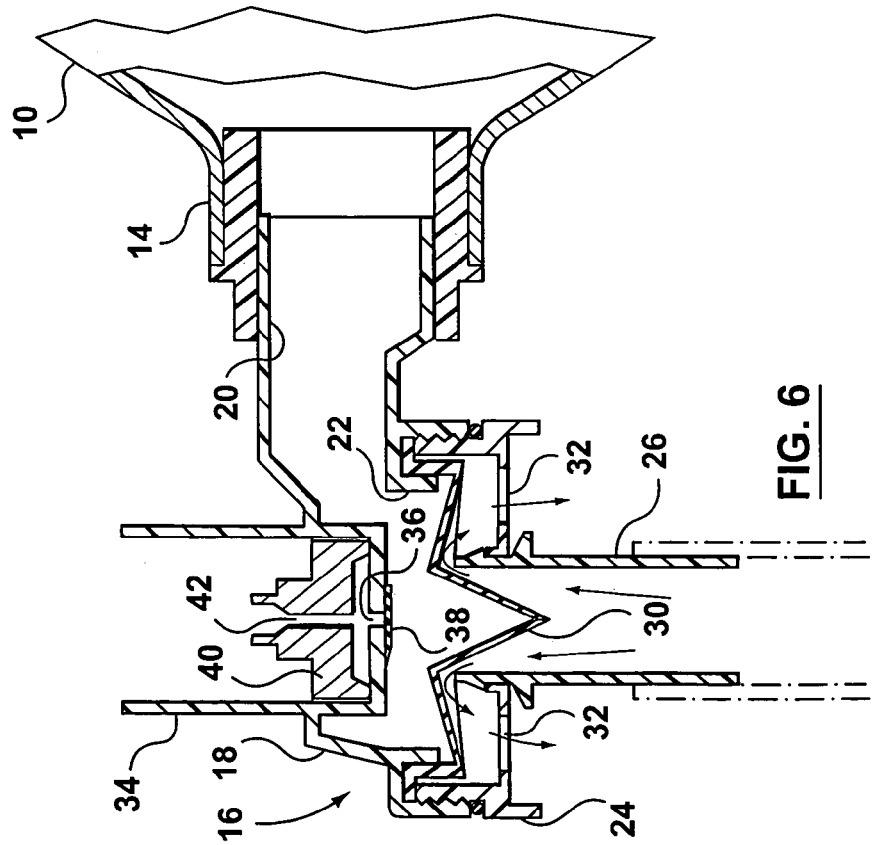
FIG. 6 is a similar view but showing the patient valve during exhalation of air by the patient.

During compression of the air bag 10 and consequent opening of duckbill valve member 30, the medication container 44 is pushed downwardly to release a predetermined dose of medication in spray form through outlet tube 46 in known manner, as shown in FIG. 7.

The medication spray opens flap valve 38 so that the medication passes directly into duckbill valve portion 30, thereby being entrained in air from the air bag passing therethrough with consequent effective delivery to the patient.

Alternatively, medication maybe supplied from a syringe by inserting the syringe needle into the central passage 42 of the connector 40.

It will be noted that the patient valve 16 causes the air from the bag 10 to turn through 90° to pass through the duck bill valve portion 30 and that the passage 42 is located so as to inject medication into the air in a direction substantially parallel to the direction of the flow of the air through the duck bill valve 30.

The advantages and other embodiments of the invention will now be readily apparent to a person skilled in the art from the foregoing description.

The invention claimed is:

1. A manually-operable resuscitator operable also to inject medication into air being supplied to a patient, said resuscitator having:
 - a resiliently compressible air bag having an inlet and an outlet, and a patient valve through which air flows in passing from the bag to the patient,
 - the patient valve having a one-way valve member through which air flows in passing from the bag to the patient,
 - the patient valve also having a passage extending from the atmosphere to the interior thereof adjacent to the one-way valve member and upstream thereof through which medication can be injected into the air as it passes from the bag to the one-way valve member, and
 - the patient valve causing air from the bag to turn through approximately 90° to pass through the one-way valve member and the passage being located so as to inject medication into the air in a direction substantially parallel to the direction of flow of the air through the one-way valve member.

2. A resuscitator according to claim 1 wherein the passage is provided with a one way valve through which the medication passes.

* * * * *